(12) United States Patent
Senegas

(10) Patent No.: US 6,761,720 B1
(45) Date of Patent: Jul. 13, 2004

(54) INTERVERTEBRAL IMPLANT

(75) Inventor: Jacques Senegas, Merignac (FR)

(73) Assignee: Spine Next, Bordeaux (FR)

( * ) Notice: Subject to any disclaimer, the term of this patent is extended or adjusted under 35 U.S.C. 154(b) by 25 days.

(21) Appl. No.: 10/110,841

(22) PCT Filed: Oct. 13, 2000

(86) PCT No.: PCT/FR00/02862
§ 371 (c)(1),
(2), (4) Date: Jul. 11, 2002

(87) PCT Pub. No.: WO01/28442
PCT Pub. Date: Apr. 26, 2001

(30) Foreign Application Priority Data

Oct. 15, 1999 (FR) .............................................. 99 13156

(51) Int. Cl.⁷ .............................................. A61B 17/70
(52) U.S. Cl. .......................................... 606/61; 606/60
(58) Field of Search .............................. 606/60, 61, 53, 606/105, 74, 90

(56) References Cited

U.S. PATENT DOCUMENTS 5,496,318 A    3/1996 Howland et al.

FOREIGN PATENT DOCUMENTS

| FR | 2 717 675 | 9/1995 |
|----|-----------|--------|
| FR | 2 775 183 | 8/1999 |

*Primary Examiner*—Cary E. O'Connor
*Assistant Examiner*—Candice C. Melson
(74) *Attorney, Agent, or Firm*—Merchant & Gould P.C.

(57) ABSTRACT

The invention relates to an intervertebral implant comprising a spacer (2) in which two opposite notches (6a, 6b) are formed suitable for receiving two respective spinus processes (26a, 26b) of two vertebrae, each notch defining two flanges (8a, 10a, 8b, 10b) each having an inside wall, and the implant also having a tie (4a, 4b) for holding said spacer on said spinus processes. Said tie is constituted by at least one strap having a portion surrounding a portion of the surface of a spinus process that is opposite from the bottom of the notch. Said implant has first fixing means (12a, 12b) formed in at least one flange (8a, 8b) for fixing a first end (18a, 18b) of said strap, and self-locking second fixing means (14a, 16a, 14b, 16b) formed in at least one other flange (10a, 10b) and through which the second end (20a, 20b) of said strap is inserted and then pulled to hold said strap (4a, 4b) in position, thereby securing said spacer (2) to said spinus processes (26a, 26b).

20 Claims, 2 Drawing Sheets

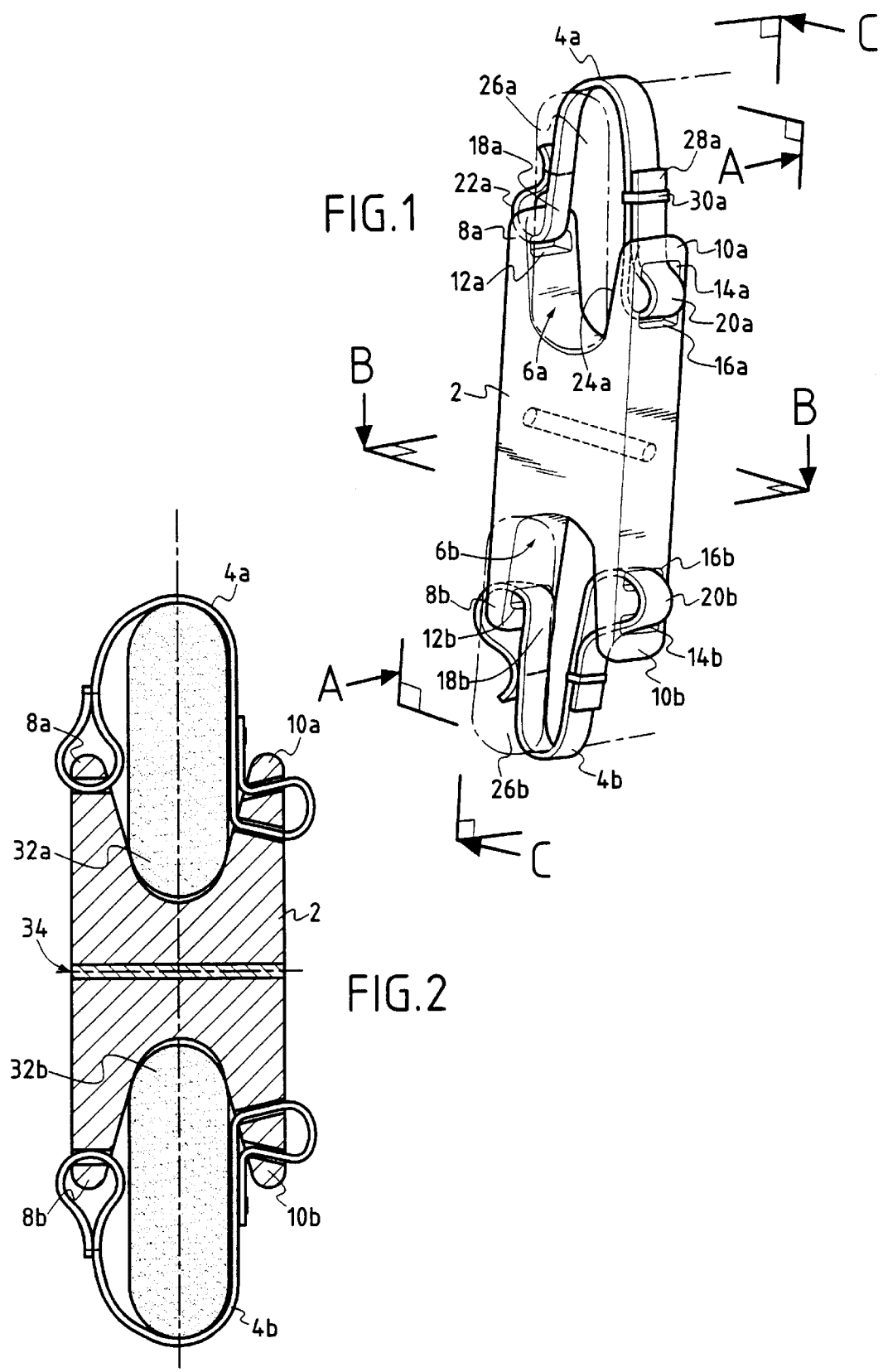

INTERVERTEBRAL IMPLANT

The present invention relates to an intervertebral implant comprising a spacer and a tie for holding the spacer between two vertebrae.

The spacer compensates for a vertebral disk when the disk is deficient and in particular it limits the extent to which the posterior portions of two vertebrae can move towards each other when the spine is extended. The posterior portions of two vertebrae coming too close together gives rise to discomfort, and in particular to pain.

When a vertebral disk has degenerated, movements of the spine can cause contact to be made between vertebrae which can pinch the roots of the nerves that come out laterally between the vertebrae.

To remedy that drawback, it is known to fix at least one spacer between two spinus processes of two consecutive vertebrae. These spinus processes project from the vertebrae in the form of knobbles on the posterior portion of the vertebral column.

Thus, by putting a spacer between two successive spinus processes, the vertebrae are prevented from coming into contact when the vertebral disk is deficient.

However, the spacer must be fixed to the vertebrae in a manner that is sufficiently rigid to keep it in position regardless of the movements of the spine, and it must be sufficiently free relative to the same vertebrae to avoid excessively stiffening the vertebral column. It is known to fix such a spacer, which has one or more through holes formed therein, by means of ligaments inserted in the holes and forming loops into which the spinus processes are engaged. That fixing system is not very rigid and it requires a large number of manipulations, thereby correspondingly increasing the time required for surgery.

An object of the present invention is to provide an intervertebral implant whose means for fixing to the spinus processes are capable of being put into place in a length of time that is relatively short compared with the prior art, and which provides fixing that is more rigid.

To achieve this object, the invention provides an intervertebral implant comprising a spacer in which two opposite notches are formed suitable for receiving the two spinus processes of two vertebrae, each notch defining two flanges each having an inside wall, the implant also having a tie for holding said spacer to said spinus processes, and the implant being characterized in that:

said tie is constituted by at least one strap having a portion surrounding a portion of the surface of the spinus process opposite from the bottom of the notch;
and in that said implant further comprises:
first fixing means formed in at least one flange to fix a first end of said strap; and
self-locking second fixing means formed in at least one other flange, the second end of said strap being inserted through said self-locking fixing means and then pulled to hold said strap in position, thereby securing said spacer to said spinus processes.

It will be understood that the spacer is inserted between two vertebrae and that each of the spinus processes extending therefrom bears against a respective opposite notch in said spacer. The various flexions of the spine give rise to each spinus process having a certain amount of mobility relative to the other, and the spacer is held in position by a strap which provides a contact area with the spinus process that is greater than that provided by a tie of the ligament type.

Consequently, the tie is held more securely to the spinus process. Furthermore, one end of the strap is fixed in one of the two flanges constituting the notch and advantageously the first fixing means comprise a slot formed through said flange, said first end of said strap being suitable for being engaged in said slot in such a manner as to form a loop whereby said first end of said strap is secured to said flange. This method of fixing is relatively easy to install. Thus, the end of the strap is fixed to said spacer by ligating the tip of the strap to a portion of its end after it has passed through said slot and a loop has been formed. This operation is performed prior to installing the spacer between two vertebrae.

The second end of the strap is fixed to said other flange via the self-locking fixing means that preferably comprise a first slot and a second slot that are parallel to each other, said slots being formed through the other flange, said second slot being situated between said first slot and the bottom of the notch such that the portion of the strap which passes through the first slot and projects from said inside wall of said other flange is pressed against the portion of the strap which penetrates into the second slot, thereby enabling the end of said strap to be locked by friction.

Advantageously, said tie has two straps and thus each notch has first fixing means in one of its flanges and self-locking fixing means formed in its other flange so as to enable two straps to be fixed, each strap being suitable for passing round a respective one of the spinus processes, whereby said spinus processes are held independently of each other.

It will be understood that the straps are suitable for being premounted so as to form a loop on each notch. The tip of the second end of each strap is then engaged in each second slot via the inside wall of each of said other flanges and is reinserted into the notch via said first slot so as to project from the inside wall of the flange.

When the spacer is inserted between the vertebrae, the spinus processes pass through the loops and fixing is finished off by pulling on the tips of the straps so as to hold said spinus processes tightly in the notches.

It will also be understood that the self-locking means are used during the tightening operation. The more the strap is tightened on the spinus process, the longer the portion of strap projecting from the inside wall of the flange that is pressed against the portion of the strap which penetrates into the second slot. Thus, the two strap portions are pinched between the inside wall of the flange and the body of the spinus process, thereby preventing said end of the strap from moving relative to the flange.

In a first embodiment, the spacer is fixed in parallel on the spinus processes by means of two separate straps.

In a second embodiment, the spacer is fixed on the spinus processes by means of a single strap.

Other features and advantages of the invention will appear on reading the following description given by way of non-limiting indication and made with reference to the accompanying drawings, in which:

FIG. 1 is a perspective view of a first embodiment of the intervertebral implant showing a spacer provided with two straps for fixing the spacer on two consecutive spinus processes;

FIG. 2 is a view of the intervertebral implant in section on plane A—A of FIG. 1, showing the position of the spinus processes relative to the spacer;

Figure 3:
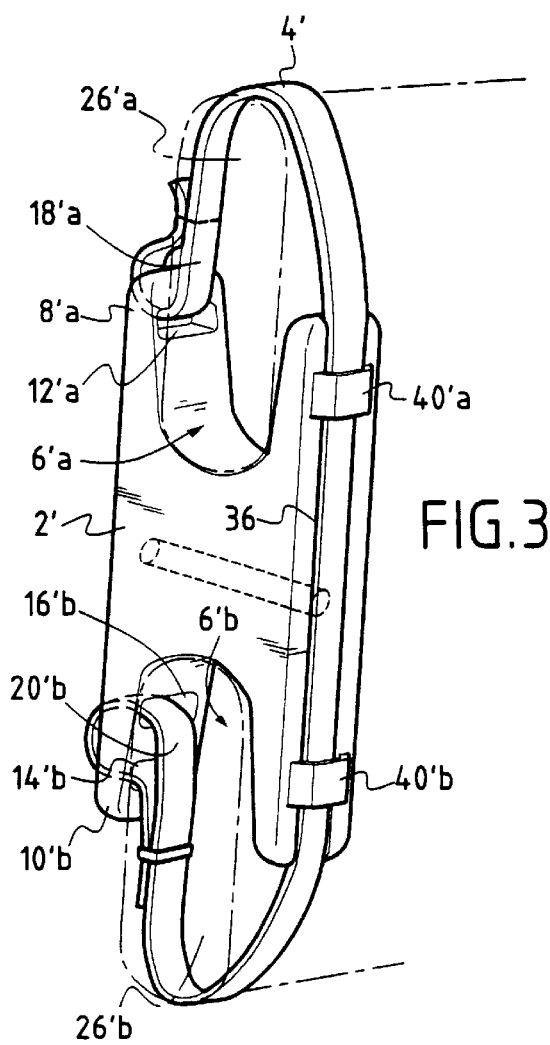
FIG. 3 is a perspective view of a second embodiment of the intervertebral implant fitted with a single strap.

With reference initially to FIG. 1, a first embodiment of the intervertebral implant is described in which the tie is constituted by two straps.

The implant comprises a spacer 2 and two straps 4a and 4b. The spacer 2 is generally in the form of a rectangular parallelepiped having two ends each having a respective notch 6a and 6b. These notches are opposite each other; they are symmetrical about a plane of symmetry B of the spacer that is perpendicular to the long sides of the parallelepiped, and their planes of symmetry C coincide. The notches define flanges 8a, 10a, 8b, 10b in which fixing means 12a, 12b, 14a, 14b, 16a, 16b are provided for fixing the ends 18a, 18b, 20a, 20b of the straps.

The fixing means 12a and 12b are identical and are provided respectively in the flanges 8a and 8b. Consequently, only the fixing of the first end 18a of the strap 4a on the flange 6a is described.

The fixing means 12a is constituted by a through hole in the flange 8a, said hole being in the form of a slot of dimensions that are at least as great as the right cross-section of the strap 4a so as to enable it to be inserted therethrough. This slot is substantially parallel to the plane of symmetry C of the notches and to the plane of symmetry B of the spacer.

A portion 22a of the end 18a of the strap 4a is inserted through the flange 8a via the slot 12a and is then folded-down onto another portion of the end of the strap so as to form a loop. The tip at the end of the strap 4a is ligated to said other portion in such a manner as to secure the end 18a of the strap 4a to the flange 8a.

The free second end 20a of the strap 4a is suitable for being moved in the plane A of the spacer, and in particular for being connected to the flange 10a disposed symmetrically to the flange 8a about the plane of symmetry C of the notches.

The self-locking fixing means 14a and 16a for locking the strap 4a in the flange 10a that is to have the second end 20a secured thereto are described below. By analogy, this description also applies to the self-locking means provided in the flange 10b which is symmetrical thereto about the plane of symmetry B of the spacer.

These fixing means of the spacer are constituted by two holes 14a and 16a in the form of slots passing through the flange 10a. These slots are parallel to each other and likewise parallel to the slot 12a formed in the first flange 8a. In addition, they have the same dimensions as said slot 12a.

The second end 20a of the strap is fixed by inserting said end through the slot 16a from the inside wall 24a of the notch 6a. The end of the strap 20a is then inserted through the slot 14a from the opposite face of the wall of the notch so as to project into the notch, and it is then pulled to press against the portion of the strap that penetrates into the slot 16a. The strap 4a, in co-operation with the notch 6a, thus constitutes a first loop in which the spinus processes 26a can be engaged.

By symmetry, the above-described fixing means are identical for the opposite notch 6b. Likewise, the second loop is made in the same manner as that described above.

In general, the straps 4a, 4b are premounted on the spacer 2 in such a manner as to enable the spacer 2 to be inserted directly between two vertebrae with the ready-formed loops being placed directly about the spinus processes. Thereafter, the tip 28a of the end 20a is pulled to tighten the spinus process 26a between the notch 6a and the strap 4a in such a manner as to lock the spacer 2 on the spinus process 26a. As a general rule, the tension in the strap 4a where it passes through the self-locking fixing means is sufficient to lock it. The way the strap 4a passes successively through the two slots 16a and 14a gives rise to large friction forces that oppose sliding of the strap 4a, in particular because of the sharp edges of the slots.

In addition, the portion of the strap which projects from the slot 14a to project from the inside wall 24a, and the portion of the strap which penetrates into the slot 16a are compressed together between the inside wall 24a of the notch 6a and the spinus process 26a, thereby accentuating the locking of the end 20a of the strap 4a to the flange 10a of the spacer 2.

The friction and compression forces exerted on the end 20a of the strap increase with increasing tightness of said strap 4a. However, if locking should be insufficient, provision can be made to fix the tip of the end 20a of the strap to the portion of the strap which passes round the spinus process 26a by means of a clip 30a.

The spacer 2 is secured in identical manner to the spinus process 26b. The spacer 2 is thus fixed between two vertebrae on the spinus processes 26a and 26b of these two vertebrae.

With reference to FIG. 2, it will be understood that when the spine is in extension, the bottom portion 32a of the spinus process 26a and the top portion 32b of the spinus process 26b tend to move towards each other and are then blocked respectively by the bottoms of the notches 6a and 6b. Thus, in the absence of a vertebral disk or in the presence of a disk that is defective, the spacer 2 limits contact between two consecutive vertebrae.

The spacer 2 is generally made of a material which is transparent to X-rays so as to make it invisible in X-ray images in order to avoid masking the organs that it is desirable to be able to visualize. Nevertheless, in order to situate the spacer relative to the spine, a transverse element that is opaque to X-rays is inserted therein, which element is sufficiently thin to avoid impeding observation of X-ray images, and is received in a central housing 34.

FIG. 3 shows a variant embodiment of the intervertebral implant in which said tie comprises a single strap 4 whose first end 18'a is fixed to said fixing means 12'a formed in a first flange 8'a of the first notch 6'a and whose second end 20,b is fixed to said self-locking fixing means 16'b, 14'b formed in the second flange 10'b of the second notch 6'b that is symmetrical to the first flange 8'a of the first notch 6'a relative to said spacer 2'.

Said spacer also has guide means formed in said spacer 2' to guide said strap 4' along the second flange of the first notch 6'a and the first flange of the second notch 6'b so that said spinus processes 26'a and 26'b are tightened simultaneously.

In this embodiment, the guide means comprise a rectilinear groove 36 formed in the outside wall of said spacer 2' in line with the second flange of the first notch 6'a and the first flange of the second notch 6'b, with the strap 4' being suitable for sliding in said groove. In order to hold the strap 4' in the groove 36, bridges 40'a and 40'b are provided over the groove 36 in register with the flanges.

This embodiment serves advantageously to enable both spinus processes to be tightened simultaneously in the notches 6'a and 6'b by a single action on the second end of the strap 4'.

Figure 4:
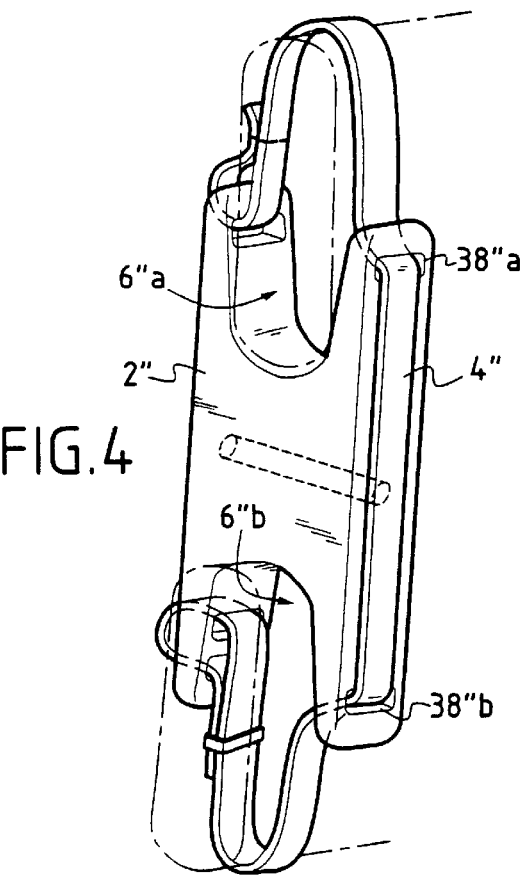
FIG. 4 is a perspective view of a third embodiment of the intervertebral implant fitted with a single strap.

FIG. 4 shows a variant embodiment of the intervertebral implant having a single strap, in which the guide means comprise a slot 38"a formed through the second flange of the first notch 6"a and a slot 38"b through the first flange of the second notch 6"b.

What is claimed is:

1. An intervertebral implant comprising:
   a spacer having two opposite notches for receiving two spinus processes of two vertebrae, each notch defining a bottom and two flanges, each having an inside wall;

a tie for holding said spacer to said spinus processes, said tie being constituted by at least one strap having first and second ends and a portion surrounding a portion of a surface of a spinus process opposite from the bottom of a notch;

first fixing means formed in at least one of said flanges to fix the first end of said strap; and self-locking second fixing means formed in at least another one of said flanges, the second end of said strap being inserted through said self-locking second fixing means and then pulled to hold said strap in position, thereby securing said spacer to said spinus processes.

2. An intervertebral implant according to claim 1, wherein the first fixing means comprise a slot formed through said flange, said first end of said strap being suitable for being engaged in said slot in such a manner as to form a loop whereby said first end of said strap is secured to said flange.

3. An intervertebral implant according to claim 1, wherein the self-locking second fixing means comprise a first slot and a second slot that are parallel to each other, said slots being formed through the other flange, said second slot being situated between said first slot and the bottom of the notch such that the portion of the strap which passes through the first slot and projects from said inside wall of said other flange is pressed against the portion of the strap which penetrates into the second slot, thereby enabling the end of said strap to be locked by friction.

4. An intervertebral implant according to claim 1, wherein each notch has first fixing means in one of its flanges and self-locking second fixing means formed in its other flange so as to enable two straps to be fixed, each strap being suitable for passing round a respective one of the spinus processes, whereby said spinus processes are held independently of each other.

5. An intervertebral implant according to claim 1, wherein a first flange of the first notch has first fixing means for fixing the first end of a strap;

wherein the second flange of the second notch, symmetrical to the first flange of the first notch about said spacer, has self-locking second fixing means for locking the second end of said strap; and wherein said spacer also includes guide means formed in said spacer to guide said strap in line with the second flange of the first notch and the first flange of the second notch whereby said spinus processes are tightened simultaneously.

6. An intervertebral implant according to claim 5, wherein the guide means comprise a slot formed through the second flange of the first notch and a slot formed through the first flange of the second notch.

7. An intervertebral implant according to claim 5, wherein the guide means comprise a rectilinear groove formed in the outside wall of said spacer in line with the second flange of the first notch and with the first flange of the second notch, and in which said strap is suitable for sliding.

8. An intervertebral implant comprising:

a spacer having two opposite notches for receiving two spinus processes of two vertebrae, each notch defining a bottom and two flanges, each flange having an inside wall;

a tie for holding said spacer to said spinus processes, said tie including at least one strap having first and second ends and a portion surrounding a portion of a surface of a spinus process opposite from the bottom of a notch;

first fixing means formed in at least one of said flanges to fix the first end of said strap; and self-locking second fixing means comprising a first slot and a second slot, said slots being formed through another one of said flanges, and said second slot being situated between said first slot and the bottom of the notch, the second end of said strap being inserted through said first and second slots and then pulled, so that the second end of said stay is locked by friction, thereby securing the spacer to said spinus processes.

9. An intervertebral implant according to claim 8, wherein the first fixing means comprise a slot formed through said at least one of said flanges, said first end of said strap being suitable for being engaged in said slot in such a manner as to form a loop whereby said first end of said strap is secured to said at least one of said flanges.

10. An intervertebral implant according to claim 8, wherein the first slot and the second slot of said self-locking second fixing means are parallel to each other, and wherein a portion of the strap which passes through the first slot and projects from said inside wall of said at least another one of said flanges, is pressed against another portion of the strap which penetrates into the second slot, thereby enabling the end of said strap to be locked by friction.

11. An intervertebral implant according to claim 8, wherein each notch has fist fixing means in one of its flanges and self-locking second fixing means formed in its other flange so as to enable two straps to be fixed, each strap being suitable for passing round a respective one of the spinus processes, whereby said spinus processes are held independently of each other.

12. An intervertebral implant according to claim 8, wherein a first flange of a first notch has first fixing mans for fixing the first end of a strap;

wherein a second flange of a second notch, symmetrical to the first flange of the first notch in relation to said spacer, has self-locking second fixing means for locking the second end of said strap; and wherein said spacer includes guide means formed in said spacer to guide said strap in line with a second flange of the first notch and a first flange of the second notch whereby said spinus processes are tightened simultaneously.

13. An intervertebral implant according to claim 12, wherein the guide means comprise a slot formed through the second flange of the first notch and a slot formed through the first flange of the second notch.

14. An intervertebral implant according to claim 12, wherein the guide means comprise a rectilinear groove formed in the outside wall of said spacer in line with the second flange of the first notch and with the first flange of the second notch, and in which said strap is suitable for sliding.

15. An intervertebral implant comprising:

a spacer having two opposite notches for receiving two spinus processes of two vertebrae, each notch defining a bottom and two flanges, each flange having an inside wall;

a tie for holding said spacer to said spinus processes, said tie including at least one strap having first and second ends and a portion surrounding a portion of a surface of a spinus process opposite from the bottom of a notch;

first fixing means formed in at least one of said flanges to fix the first end of said strap; and self-locking second fixing means comprising a first slot and a second slot that are parallel to each other, said slots being formed through at least another one of said flanges, and said second slot being situated between said first slot and the bottom of the notch such that a portion of the strap which passes through the first slot and projects from said inside wall of said another one of said flanges is pressed against a portion of the strap which penetrates into the second slot, thereby enabling the end of said strap to be locked by friction and securing said spacer to said spinus processes.

16. An intervertebral implant according to claim 15, wherein the first fixing means comprise a slot formed through said at least one of said flanges, said first end of said strap being suitable for being engaged in said slot in such a manner as to form a loop whereby said first end of said strap is secured to said at least one of said flanges.

17. An intervertebral implant according to claim 15, wherein each notch has first fixing means in one of its flanges and self-locking second fixing means formed in its other flange so as to enable two straps to be fixed, each strap being suitable for passing round a respective one of the spinus processes, whereby said spinus processes are held independently of each other.

18. An intervertebral implant according to claim 15, wherein a first flange of a first notch has first fixing means for fixing the first end of a strap;

wherein a second flange of a second notch, symmetrical to the first flange of the first notch in relation to said spacer, has self-locking second fixing means for locking the second end of said strap; and guide means are formed in said spacer to guide side strap in line with a second flange of the first notch and a first flange of the second notch whereby said spinus processes are tightened simultaneously.

19. An intervertebral implant according to claim 18, wherein the guide means comprise a slot formed through the second flange of the first notch and a slot formed through the first flange of the second notch.

20. An intervertebral implant according to claim 18, wherein the guide means comprise a rectilinear groove formed in the outside wall of said spacer in line with the second flange of the first notch and with the first flange of the second notch, and in which said strap is suitable for sliding.

\* \* \* \* \*